United States Patent [19]

Koosmann

[11] Patent Number: 4,611,492
[45] Date of Patent: Sep. 16, 1986

[54] MEMBRANE TYPE NON-INTRUSIVE ICE DETECTOR

[75] Inventor: Mark R. Koosmann, Corcoran, Minn.

[73] Assignee: Rosemount Inc., Eden Prairie, Minn.

[21] Appl. No.: 606,663

[22] Filed: May 3, 1984

[51] Int. Cl.⁴ .................................................. G01N 29/00
[52] U.S. Cl. .................................... 73/579; 73/590; 340/582
[58] Field of Search .............. 73/590, 579, 576, 583, 73/702, 170 R; 340/582

[56] References Cited

U.S. PATENT DOCUMENTS

| | | | |
|---|---|---|---|
| 2,414,756 | 1/1947 | May | 340/582 |
| 2,800,647 | 7/1957 | Baerwald et al. | 340/582 |
| 3,240,054 | 3/1966 | Roth | 73/576 |
| 3,341,835 | 9/1967 | Werner et al. | 340/582 |

FOREIGN PATENT DOCUMENTS 506843  7/1938  United Kingdom .

Primary Examiner—Anthony V. Ciarlante
Attorney, Agent, or Firm—Kinney & Lange

[57] ABSTRACT

An ice detector of the vibrating element type comprises a tube that vibrates along its longitudinal axis, and is driven by an excitation coil at the natural frequency of the tube is sealed by a diaphragm which has a surface exposed to an air stream in which icing is to be sensed. The exposed diaphragm surface is deflectable during vibration of the tube at a flexible support portion of the diaphragm. As ice accumulates on the exposed surface of the flexible support the spring rate or flexibility of the flexible support changes, thereby changing the natural frequency of the vibration of the tube section. The changes in the natural frequency are sensed to determine that ice is accumulating. The diaphragm is of low mass, and small so that stiffness of small amounts of ice significantly changes the spring constant of the flexible support and the diaphragm is shaped to conform to adjacent aerodynamic surfaces.

8 Claims, 3 Drawing Figures

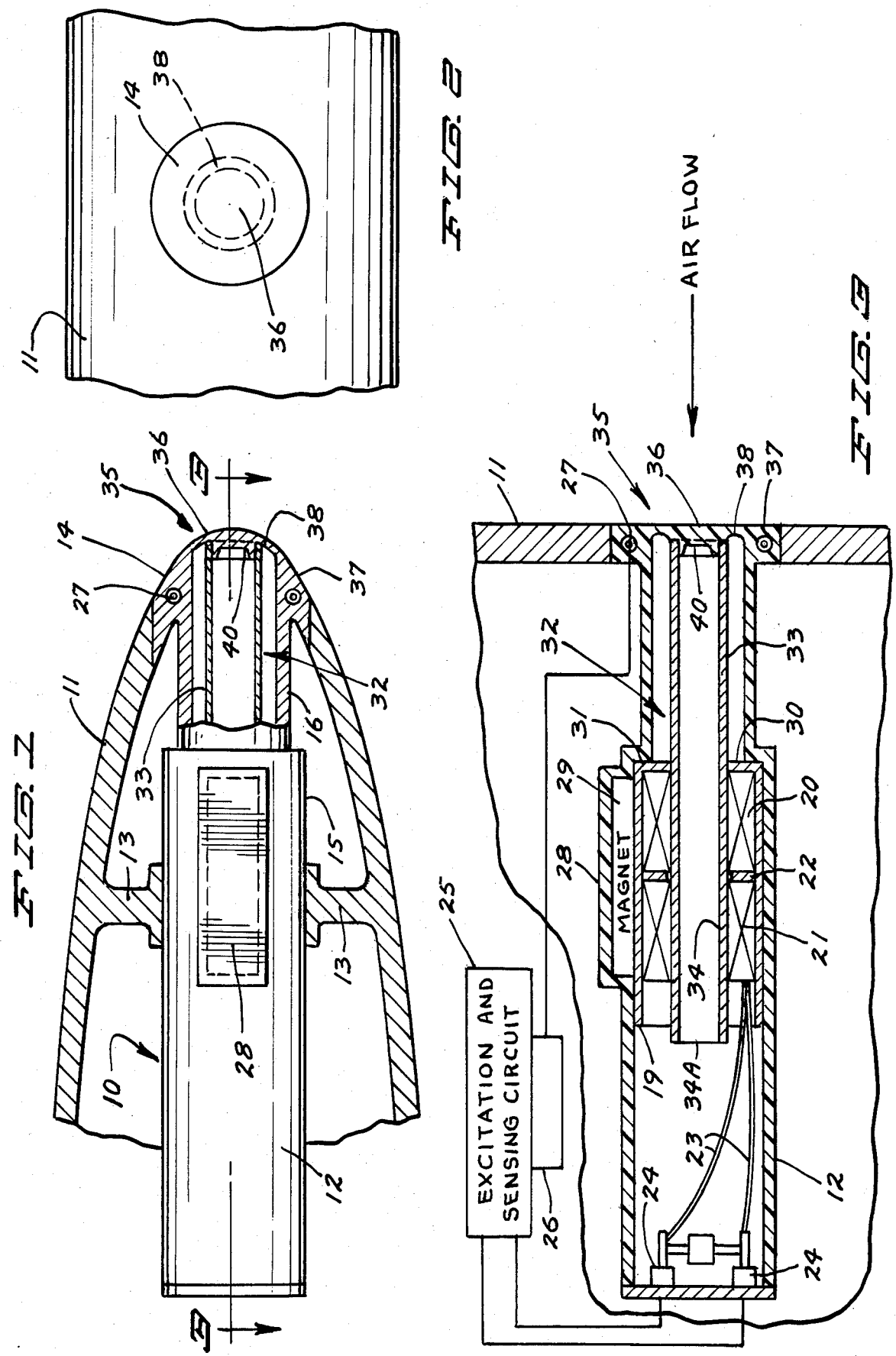

MEMBRANE TYPE NON-INTRUSIVE ICE DETECTOR

BACKGROUND OF THE INVENTION

1. Field of the Invention

The present invention relates to ice detectors of the vibrating type, and in particular detectors having a small sensing surface which does not intrude substantially into the air stream being sensed and which may be made to conform to the external shape of the mounting surface.

2. Description of the Prior Art

In the prior art a vibrating type ice detector which changes the natural frequency upon accumulation of ice on the sensing probe is shown in U.S. Pat. No. 3,341,835. This patent has a tube supported substantially at a midpoint, which forms a node of vibration, and the tube is driven with a coil to vibrate axially between the node and its opposite ends at its natural frequency. The vibration is a minute lengthening and shortening of the two tube sections between the node and the respective ends. The frequency of vibration is sensed by a feedback coil. Ice accumulation on the exposed portion of the probe causes a change in natural frequency, as opposed to a dampening of amplitude of vibration, and this change in frequency is sensed as an indication of ice accumulation.

The circuitry used for driving the tube to its natural frequency, that is setting up longitudinal vibration between a mounting node and opposite ends of the tube, operates on the same principle as in the present application and the principle of sensing the change in frequency caused by ice accumulation is also the same. However, in U.S. Pat. No. 3,341,835 the probe protrudes substantially into the air stream, causing drag and the possibility of mechanical damage, and also forming a radar reflective target.

In the present device, the sensing surface is non-intrusive, and incorporates different physical principles which result in a change in frequency of vibration of the tube.

A mechanical displacement type ice detector sensor using a diaphragm is shown in U.S. Pat. No. 2,414,756. In this particular instance the diaphragm does not protrude into the air stream, as such, but the sensing is done by driving the diaphragm to deflect in opposite directions. Operation is carried out by measuring the dampening of displacement occasioned by ice accumulation. Frequency sensing is not used, and the structure disclosed in U.S. Pat. No. 2,414,756 has to be quite large so that there is a substantial change in mass of the system when ice accumulates on a diaphragm before accurate output readings can be obtained. This then has the problem of large size and low sensitivity to small accumulations of ice, and there is a requirement that there be substantial displacement of the diaphragm. Further, shaping this type of diaphragm to conform to the shape of the surface in which the ice detector is mounted is not practical in that the diaphragm has to be substantially planar for operation.

A frequency sensitive ice detector which has a large area, tapered disc covered with a fabric that is exposed to the formation of ice is shown in U.S. Pat. No. 2,800,647. In this patent an assembly stack of crystal plates forms a vibrating column supporting the disc, and the changes in resonant frequency of the vibrating column are sensed for determining ice accumulation.

The fabric outer cover forms an ice collecting surface, and the mass of ice on the surface is sensed by the vibrating system, due to natural frequency changes because of the change in mass on the fabric.

It is pointed out that the fabric area in this patent can form a smooth continuation of adjacent portions of the extended mounting surface. However, the sensor requires quite a large surface area; the use of fabric, which is not suitable for high performance aircraft; and a complex mounting assembly.

U.S. Pat. No. 3,240,054 also shows an ice detector that has a surface that collects ice, and depends upon the vibrating of an elastic diaphragm which changes in stiffness upon ice accumulation.

The device shown depends on the flexural stiffness of the entire diaphragm and diaphragms cannot be shaped to conform to a curved surface. U.S. Pat. No. 3,240,054 does, however, teach that the stiffness of ice can change resonant frequencies of elastic members that are being used for ice detectors.

An exposed diaphragm used for sensing ice formation is shown in British Specification No. 506,843, but again the diaphragm is motion sensitive, and the dampening of displacement by the mass of ice accumulated is necessary for providing an output.

Other non-intrusive ice detectors have been developed which depend upon sensing of the mass of ice, but one of the problems in having a very small sensor surface is that the mass of the ice is not very great in a small area, until accumulation is substantial, and thus the ability to sense small accumulations to give an early indication of ice formation is reduced.

SUMMARY OF THE INVENTION

The present invention relates to an ice detector which has a small exposed diaphragm surface and which can be conformed to a curved shape that forms a continuation of the surface on which ice formation is to be detected. The surface used for sensing ice does not intrude into the air stream and eliminates additional drag. The sensor is then less likely to be sensed by radar. The diaphragm has an outer edge support, a central portion and a flexible wall portion that mounts the center portion to the outer edge. The center portion is vibrated by suitable means (as disclosed a vibrating tube) at a natural frequency which is sensed and which changes due to changes in spring constant of the flexible wall portion as ice accumulates.

The device of the present invention permits sensing small accumulations of ice, because the ice is stiff and causes a substantial change in spring constant of the flexible wall, which alters the natural frequency of the vibrating tube. The unit can be deiced conventionally, and because it is small and the shape of the center portion is alterable, the diaphragm is made to conform to contours or other configurations of an airfoil or other surfaces on which it is to be mounted. It has a wide range of uses including meteorogical devices, air vehicles and commercial devices where formation of ice is to be sensed.

BRIEF DESCRIPTION OF THE DRAWINGS

FIG. 1 is a fragmentary vertical sectional view through a typical airfoil section such as a wing of an air vehicle, and having a sensor made according to the FIG. 2 is a front view of the device of FIG. 1; and FIG. 3 is a sectional view taken as on line 3—3 in FIG. 1.

DETAILED DESCRIPTION OF THE PREFERRED EMBODIMENTS

An ice detector indicated generally at 10 is mounted onto a surface, such as a wing 11 on which ice may accumulate, and where such accumulation of ice is to be sensed. The mounting surface may be any surface in any location where ice will form. Air vehicle surfaces, and turbine inlets are two types of surfaces where the present invention finds use. The ice detector 10 includes an outer housing 12 which is attached with respect to the wing 11 with suitable supports illustrated schematically at 13, and which has an end member 14 mounted in an opening in the surface, such as a wing, and tightly sealed around its periphery with respect thereto. As can be seen in cross section in FIG. 1, the leading end of the ice detector end member 14 can be contoured to conform to the shape of the surface on which it is mounted.

The housing 12 may be made of either a suitable plastic or metal and includes an enlarged section 15, and a smaller section 16 which is attached to the end portion 14. The enlarged section 15 mounts a coil tube 19 in which a drive coil 20 is mounted adjacent one end. A sensing or feedback coil 21 is mounted coaxial with the coil 20 in the coil tube 19 and is spaced therefrom by a washer 22, which may be made of suitable material such as copper, to effectively magnetically decouple the two coils.

Suitable lead wires 23 lead from the coils to terminals 24, and the terminals are connected to excitation and sensing circuitry of conventional design indicated at 25. As part of this sensing circuitry, there are means to determine changes in natural frequency indicated at 26 which will control power to a heater wire shown at 27 in the outer end member 14, to remove ice that has accumulated after the ice has accumulated on the sensor sufficiently to be detected. The heater 27 causes previously accumulated ice to melt and fall off. The heater then is shut off so that the ice detector is capable of detecting continuing or recurring icing conditions. A mounting receptacle 28 formed on housing 12 mounts a permanent magnet 29 adjacent drive coil 20 and feedback coil 21.

A support 30 is mounted at a shoulder 31 formed in the housing 12, between the sections 15 and 16. Support 30 is an annular washer to which a vibrating tube 32 is fixedly attached on the inner surface of support 30. The support 30 is a vibration termination support, forming a node on the tube 32. The tube 32 is made of a suitable magneto strictive material capable of being driven by the drive coil 20, for vibration in longitudinal direction, that is along the axis of tube 32. Permanent magnet 29 elongates tube 32 such that when tube 32 is driven by drive coil 20, the vibration is substantially sinusoidal because tube 32 is not compressed, but vibrated about a state of elongation. With the support 30 in place, a first section 33 of the tube 32 extends from the support 30 to the member 14, and a second section 34 of the tube extends from the support 30 in opposite direction toward an open end of the tube indicated at 34A. The two tube sections vibrate from the center mounting plane defined by support 30 outwardly under excitation from drive coil 20 acting directly on tube section 34.

The tube sections vibrate by elongating and compressing from an elongated state slightly in the axial direction. The support 30 forms a vibration node along the diametral plane passing through the support 30.

The first outer end tube section 33, as shown, is coupled in a suitable manner to a vibrating diaphragm 35 formed as part of the member 14, and having a central portion 36 forming a sleeve 40 that fits inside the tube section 33. The sleeve 40 is fixed to the tube section 33 in a suitable manner so axial vibration of the tube section causes deflection of the central portion 36 of diaphragm 35. It should be noted that the end of tube section 40 is terminated along a plane perpendicular to its axis and is not curved or shaped to conform to the outer surface of the wing.

The central portion 36 of the diaphragm 35 is therefore supported for movement with the tube section 33. The central portion 36 is connected to an outer peripheral support portion 37 of the diaphragm 35 through an annular spring or flexible connector portion 38 which is of reduced thickness from the center portion 36. The flexible connector portion 38 forms an annular spring hinge all around the diaphragm center portion 36 in the preferred embodiment, to spring load the center portion 36 relative to its peripheral support portion 37 so that deflecting movement of the center portion of the diaphragm will be under a spring load by bending the spring wall section 38. The flexible connector portion 38 may form a flexible annular hinge around the diaphragm center portion 36 to provide for free deflecting movement of the center portion of the diaphragm, rather than providing any spring load.

The diaphragm flexible wall section 38 is preferably in the range of 0.005 inches to 0.025 inches thick, having a radial length of 0.010 to 0.050. It may be of a suitable light weight elastic non radar reflective plastic material such as a polycarbonate or Delrin, or if desired, it may be made of a metal.

When the ice detector is operated, it is driven by the drive coil 20 to its natural frequency so that as the tube sections 33 and 34 vibrate longitudinally the tube sections extend and contract in length from the diametral plane at the support 30, which forms the node of vibration. This vibration in turn will deflect the diaphragm central portion 36 at the natural frequency of the assembly of the tube section 33. The natural frequency of the tube section 33 depends upon the spring constant of the flexible wall portion 38 as well as the spring constant of the tube section 33 and the masses of the tube section 33 and the central portion 36 of the diaphragm 35.

Thus the natural frequency $f_{n1}$ of the tube section 33 and diaphragm 35 is governed by the equation:

$$f_{n1} = \frac{1}{2\pi} \sqrt{\frac{K_1 + K_2}{M_1 + \frac{M_2}{3}}} \qquad \text{(Equation 1)}$$

Where
$K_1$ = Spring constant of the tube section 33.
$K_2$ = Spring constant of the diaphragm flexible wall portion 38.
$M_1$ = Mass of the center diaphragm portion 36.
$M_2$ = Mass of the tube section extending from the support 31 to the diaphragm portion 36.

The natural frequency $f_{n2}$ of the tube section 34 is governed by the equation:

$$f_{n2} = \frac{1}{2\pi} \sqrt{\frac{K_3}{\frac{M_3}{3}}} \qquad \text{(Equation 2)}$$

Where $K_3$ = Spring constant of the tube section 34.
$M_3$ = Mass of the tube section 34.

In use, the natural frequency of the two tube sections 33 and 34 should be approximately equal, and when the drive coil drives the tube section 33 at its natural frequency, as sensed through the feedback coil and conventional circuitry, the tube section 34 near the coils vibrates longitudinally, and this vibration is transmitted across the support 30 at the tube node, to the tube section 33 to the sensing surface comprising flexible wall portion 38. As the ice forms on the sensing surface, the stiffness of the flexible wall portion 38 increases, and while the mass $M_1$ also increases, the ice is very stiff so that the effect of the stiffness of the wall portion 38 increases at a greater rate than the effect of mass $M_1$ and the natural frequency $f_{n1}$ increases. This also results in an increase in $f_{n2}$, and this change in frequency is accommodated by a slight shifting of the actual node of vibration along the longitidinal axis of the tube. The feedback coil 21 senses the change in natural frequency and the shift in frequency is sensed at the external circuit 25 to provide an indication that ice is forming. The circuit output can be used for activating warning signals or for turning on remote deicing equipment the rate of icing also can be determined by sensing the changes in natural frequency during an elapsed time. Also, the circuit can be used for initializing power for energizing the heater 27 for deicing the ice detector. The heater 27 operates substantially as described in U.S. Pat. No. 3,341,835.

The natural frequency of the tube section 33 and diaphragm 35 as seen in Equation 1 increases with increase in the spring constant of the flexible wall portion 38 caused by ice accumulation. Ice accumulation on diaphragm 35 increases the mass of the center diaphragm portion 36, which by itself tends to cause a slight decrease in natural frequency. However, the modulus of elasticity of ice shortly after formation is on the order $1 \times 10^6$ psi which leads to significant changes in spring constants when compared to the spring constants of tube section 33 and flexible wall portion 38. Increases in spring constant cause the natural frequency to increase. Experiments in a wind tunnel have shown that the natural frequency increases with ice accumulation, thus confirming that the tendency to increase in natural frequency caused by increased spring constant is more significant than the tendency to decrease in natural frequency caused by increased mass.

The following example is submitted for illustration purposes. The density of ice is approximately 0.0324 lb/in$^3$. For an ice accumulation of 0.025 in. over a diaphragm area of approximately 0.44 in$^2$, the mass of ice is approximately 0.00009 lbs. In Equation 1, where $M_2$, the mass of the tube section 33 extending from the support 30 to the diaphragm portion 36 is approximately 0.003 lbs., and the mass of the center diaphragm portion 36 is approximately 0.00030 lbs, the percentage change in the denominator of Equation 1 due to increase in mass from ice accumulation is less than 7%. The spring constant $K_1$ of the tube section 33 is approximately 340,000 lb/in and that of the flexible wall portion 38 is approximately 4600 lb/in. The percent change in the numerator of Equation 1 due to an accumulation of 0.025 in. of ice, is greater than 40%. Thus, as evidenced by experimental results, the change in spring constant due to ice accumulation has a much greater effect on the natural frequency than the mass of the accumulated ice.

Because the ice detection is done through a frequency change occasioned by the stiffness change in the flexible wall portion 38, the detector is sensitive to small accumulations of ice, and is not dependent upon substantial mass changes. This makes the detector adaptable to be small and non-intrusive. Accumulation of ice on the center diaphragm portion 36 does not significantly affect the frequency of vibration. The center diaphragm portion may be shaped to conform to the surface of the member to which it is mounted such that continuity of radar profile and aerodynamic surface is maintained.

What is claimed is:

1. An ice detector adapted for mounting on a wall having a curved outer surface, said ice detector comprising a disphragm member adapted to be exposed with such wall to an air stream in which ice is to be detected, said diaphragm member having a center portion, an outer edge support portion, and a flexible wall portion extending between the outer edge support portion and the center portion, said flexible wall portion permitting deflecting movement of the center portion in direction generally normal to the diaphragm member; the diaphragm member being curved to form a smooth continuation of the curved outer surface of a wall on which the diaphragm member is mounted, means connected to the center portion of the diaphragm member to vibrate the center portion and having a mass that is selected to cause the natural frequency of vibration of the means to vibrate and the connected center portion of the diaphragm member to be dependent upon the flexibility of said flexible wall portion between the center portion and the outer edge support portion of said diaphragm member; and means to sense changes in natural frequency of said means to vibrate upon change in flexibility of the flexible wall portion due to stiffness of ice accumulating on said diaphragm member.

2. The ice detector according to claim 1 wherein said flexible wall portion comprises a reduced thickness section between the outer edge support portion and the center portion.

3. The apparatus as specified in claim 2 wherein said flexible wall portion is an annular wall section surrounding the center portion.

4. An ice detector comprising a small diaphragm member exposed to an air stream in which ice is to be detected, said diaphragm member having a center portion, an outer edge support portion, and a flexible wall portion extending between the outer edge support portion and the center portion, said flexible wall portion permitting deflecting movement of the center portion in direction generally normal to the diaphragm member; means connected to the center portion for vibrating the center portion of the diaphragm member and having a mass that is selected to cause the natural frequency of vibration of the connected center portion and the means for vibrating to be dependent upon the flexibility of said flexible wall portion between the center portion and the outer support edge portion of said diaphragm member wherein said means for vibrating said center portion comprising a tube member positioned on a side of said diaphragm member opposite from the airstream, a nodal support for supporting said tube member and dividing the tube member into first and second tube sections, the first tube section extending toward the diaphragm member and having its outer end connected to the center portion of said diaphragm member, and the second tube section extending in direction from said nodal support away from said diaphragm member, said first and second tube sections having substantially the same natural frequency of vibration in direction along the longitudinal axis, means for exciting the first and second tube sections into vibration at a natural frequency and for detecting such frequency of vibration, whereby changes in the natural frequency of one of the first and second tube sections results in an indication of change of frequency in the other tube section; and means to sense changes in natural frequency of said means to vibrate upon change in flexibility of the flexible wall portion due to stiffness of ice accumulating on said diaphragm member.

5. The apparatus as specified in claim 4 wherein said outer edge support portion comprises a peripheral member surrounding the center portion, and heater means mounted in said peripheral member.

6. The apparatus as specified in claim 4 wherein the mass of the first tube section and the connected center portion are selected in relation to the spring constant of the flexible wall portion so that the natural frequency of the first tube section and the connected center portion of the diaphragm member is affected by the stiffness of the ice forming on the diaphragm member a significantly greater proportional amount than the mass of such ice which forms on the diaphragm.

7. The apparatus of claim 6 wherein the natural frequency of the tube sections are substantially governed by the following equations:

$$f_{n1} = \frac{1}{2\pi} \sqrt{\frac{K_1 + K_2}{M_1 + \frac{M_2}{3}}}$$

$$f_{n2} = \frac{1}{2\pi} \sqrt{\frac{K_3}{\frac{M_3}{3}}}$$

wherein
$f_{n1}$ is the natural frequency of the first tube section
$K_1$ is the spring constant of the first tube section
$K_2$ is the spring constant of the flexible wall portion.
$M_1$ is the mass of the center portion.
$M_2$ is the mass of the first tube section.
$f_{n2}$ is the natural frequency of the second tube section
$K_3$ is the spring constant of the second tube section
$M_3$ is the mass of the second tube section.

8. An ice detector for mounting with respect to a wall having an outer surface exposed to an airstream in which formation of ice is to be detected comprising a diaphragm member adapted to be mounted on the wall and having an outer surface in the airstream, said diaphragm member having a center portion, an outer edge support portion, and a spring wall portion extending between the outer edge support portion and the center portion, said spring wall portion permitting deflecting movement of the center portion under spring load in a first direction axis;

a housing adapted to be mounted with respect to the wall and positioned on a side of said diaphragm member opposite from the airstream;

a tube member;

a support mounting said tube member to the housing to form a nodal support for the tube member and dividing the tube member into two vibrating tube sections, one of said tube sections extending from the nodal support toward the diaphragm member and having the outer end connected to the center portion of said diaphragm member for causing deflecting movement of the center portion along the first direction axis, said first direction axis being generally parallel to the orientation of the longitudinal axis of the tube member, and the other of said tube sections extending in direction from said nodal support away from said diaphragm member, said two tube sections having substantially the same natural frequency of vibration in direction along the longitudinal axis;

means for exciting the tube sections into vibration along the longitudinal axis at a natural frequency, and for detecting such frequency of vibration, whereby changes in the natural frequency of one of the tube sections results in an indication of change of frequency in the other tube section;

the center portion of said diaphragm vibrating with the first tube section, said first tube section and center portion being of a combined mass that is selected to cause the natural frequency of vibration of the first tube section to be dependent upon the spring constant of said spring wall portion between the center portion and the outer support portions of said diaphragm member; and means to sense changes in natural frequency of said tube sections upon change in spring constant of the spring wall portion due to stiffness of ice accumulating on the outer surface of said diaphragm member.

* * * * *